United States Patent
Aussant et al.

(10) Patent No.: US 10,398,632 B2
(45) Date of Patent: *Sep. 3, 2019

(54) CAPSULE COMPOSITION

(71) Applicant: GIVAUDAN SA, Vernier (CH)

(72) Inventors: Emmanuel Aussant, Paris (FR); Addi Fadel, Paris (FR); Ian Michael Harrison, Poissy (FR); Christian Quellet, Bienne (CH); Ewelina Burakowska-Meise, Mannheim (DE); Wolfgang Denuell, Mannheim (DE); Thomas Soltys, Ludwigshafen (DE)

(73) Assignee: GIVAUDAN S.A., Vernier (CH)

( * ) Notice: Subject to any disclaimer, the term of this patent is extended or adjusted under 35 U.S.C. 154(b) by 22 days.

This patent is subject to a terminal disclaimer.

(21) Appl. No.: 15/515,478

(22) PCT Filed: Oct. 27, 2015

(86) PCT No.: PCT/EP2015/074813
§ 371 (c)(1),
(2) Date: Mar. 29, 2017

(87) PCT Pub. No.: WO2016/071151
PCT Pub. Date: May 12, 2016

(65) Prior Publication Data
US 2018/0228702 A1  Aug. 16, 2018

(30) Foreign Application Priority Data

Nov. 7, 2014 (EP) .................................... 14290337

(51) Int. Cl.
| | |
|---|---|
| *A61K 8/11* | (2006.01) |
| *A61Q 13/00* | (2006.01) |
| *A61Q 15/00* | (2006.01) |
| *A61K 8/84* | (2006.01) |
| *C11D 3/50* | (2006.01) |
| *A61K 8/25* | (2006.01) |
| *A61K 8/73* | (2006.01) |
| *A61K 8/81* | (2006.01) |

(52) U.S. Cl.
CPC .................. *A61K 8/11* (2013.01); *A61K 8/25* (2013.01); *A61K 8/731* (2013.01); *A61K 8/8176* (2013.01); *A61K 8/84* (2013.01); *A61Q 13/00* (2013.01); *A61Q 15/00* (2013.01); *C11D 3/505* (2013.01); *A61K 2800/412* (2013.01); *A61K 2800/624* (2013.01); *A61K 2800/652* (2013.01)

(58) Field of Classification Search
CPC . A61K 8/11; A61K 8/25; A61K 8/731; A61K 8/8176; A61K 8/84; A61K 2800/412; A61K 2800/652; A61K 2800/624; A61Q 13/00; A61Q 15/00; C11D 3/505
See application file for complete search history.

(56) References Cited

U.S. PATENT DOCUMENTS

| | | | |
|---|---|---|---|
| 3,792,068 A | 2/1974 | Luedders et al. | |
| 4,193,889 A | 3/1980 | Baatz et al. | |
| 4,489,017 A | 12/1984 | Alberts et al. | |
| 5,225,118 A | 7/1993 | Juang et al. | |
| 5,342,556 A | 8/1994 | Traeubel et al. | |
| 5,635,166 A * | 6/1997 | Galleguillos | A61K 8/042 424/66 |
| 6,248,364 B1 | 6/2001 | Sengupta et al. | |
| 6,326,349 B1 | 12/2001 | Helminger et al. | |
| 8,650,660 B2 | 2/2014 | Shi et al. | |
| 2003/0101606 A1 | 6/2003 | Li | |
| 2003/0157170 A1 | 8/2003 | Liggins et al. | |
| 2004/0034162 A1 | 2/2004 | Laas et al. | |
| 2005/0031565 A1 | 2/2005 | Prud'Homme et al. | |
| 2005/0238598 A1 | 10/2005 | Aubert et al. | |
| 2005/0271735 A1 | 12/2005 | Stover et al. | |
| 2007/0078071 A1* | 4/2007 | Lee | A61K 8/11 510/130 |
| 2007/0202063 A1* | 8/2007 | Dihora | A61K 8/11 424/70.1 |
| 2008/0132437 A1* | 6/2008 | Zhang | C11D 1/667 510/102 |
| 2008/0194454 A1 | 8/2008 | Morgan et al. | |
| 2008/0221003 A1 | 9/2008 | Meine et al. | |
| 2010/0168251 A1 | 7/2010 | Warr et al. | |
| 2010/0196484 A1 | 8/2010 | Aubrun et al. | |
| 2011/0071064 A1 | 3/2011 | Lei et al. | |

(Continued)

FOREIGN PATENT DOCUMENTS

| | | |
|---|---|---|
| EP | 0537467 A1 | 9/1992 |
| EP | 1693104 A1 | 8/2006 |

(Continued)

OTHER PUBLICATIONS

International Search Report and Written Opinion of the International Searching Authority for corresponding application PCT/EP2015/074813 dated Dec. 17, 2015.

H. B. Scher, "Controlled Release Pesticides", Water-Soluble Polymers: Synthesis, Solution Properties and Applications, American Chemical Society, Washington, DC, US, Jan. 1, 1997, pp. 126-144.

M.W. Keller, et al., "Mechanical Properties of Microcapsules Usid in a Self-Healing Polymer", Experimental Mechanics, vol. 46, pp. 725-733, 2006.

(Continued)

*Primary Examiner* — Robert S Cabral
(74) *Attorney, Agent, or Firm* — Norris McLaughlin PA

(57) ABSTRACT

An encapsulated perfume composition for use in personal care products adapted to be applied to, and left on, the skin or hair of a human or animal subject, said encapsulated perfume composition comprising one or more polyurea capsules having a volume average diameter of 20 to 90 microns, and a capsule shell weight, which is 5 to 40% based on the total weight of the capsules.

13 Claims, No Drawings

(56) References Cited

U.S. PATENT DOCUMENTS

| | | |
|---|---|---|
| 2011/0077188 A1 | 3/2011 | Ouali et al. |
| 2011/0212144 A1 | 9/2011 | Lemoine et al. |
| 2011/0268778 A1 | 11/2011 | Dihora et al. |
| 2014/0331414 A1 | 11/2014 | Bone |

FOREIGN PATENT DOCUMENTS

| | | |
|---|---|---|
| EP | 1837073 A1 | 9/2007 |
| EP | 2179719 A1 | 4/2010 |
| EP | 2181691 A1 | 5/2010 |
| EP | 21818691 A1 | 5/2010 |
| EP | 2221039 A1 | 8/2010 |
| EP | 2426172 A1 | 3/2012 |
| EP | 2648211 A1 | 10/2013 |
| GB | 1371179 | 10/1974 |
| WO | 9845036 A1 | 10/1998 |
| WO | 0194001 A2 | 12/2001 |
| WO | 0249590 A2 | 6/2002 |
| WO | 03066209 A1 | 8/2003 |
| WO | 2006018694 A1 | 2/2006 |
| WO | 2007004166 A1 | 1/2007 |
| WO | 2007096592 A1 | 8/2007 |
| WO | 2010070602 A2 | 6/2010 |
| WO | 2011154893 A1 | 12/2011 |
| WO | 2011160733 A1 | 12/2011 |
| WO | 2011161229 A1 | 12/2011 |
| WO | 2011161265 A2 | 12/2011 |
| WO | WO-2011154893 A1 * 12/2011 | ............ B01J 13/16 |
| WO | 2012107323 A1 | 8/2012 |
| WO | 2013079435 A1 | 6/2013 |
| WO | 2013092375 A1 | 6/2013 |
| WO | 2013092958 A1 | 6/2013 |
| WO | 2014064255 A2 | 5/2014 |
| WO | 2014187874 A1 | 11/2014 |

OTHER PUBLICATIONS

Z. Zhang, et al., "Mechanical strength of single microcapsules determined by a novel micromanipulation technique", Journal of Microencapsulation, vol. 16, pp. 117-124, 1999.

M. Yanhong, et al., "The effect of different soft segments on the formation and properties of binary core microencapsulated phase change materials with polyurea/polyurethane", Journal of Colloid and Interface Science, vol. 392, pp. 407-414, 2013.

* cited by examiner

CAPSULE COMPOSITION

This is an application filed under 35 USC 371 of PCT/EP2015/074813 filed 27. Oct. 2015, and which in turn was based on EP 14290337.6 filed 7. Nov. 2014. The present application claims all available priority benefit to the foregoing applications, and also herein incorporates by reference the entirety of their disclosures.

The present invention is concerned with an encapsulated perfume composition, comprising one or more core-shell capsules, wherein the core contains a perfume, and the shell contains a polyurea resin (hereinafter "polyurea capsules"). The invention also relates to consumer products containing said composition.

Encapsulated perfume compositions are known in the art. They may be formed by a process of coating small solid particles or liquid droplets in a thin film of shell material. Although virtually any coating material, conceptually at least, is a candidate capsule shell material, in practice, for commercial and regulatory reasons, to-date, there are relatively few materials that have been used in commercial products. Capsule shell material selection is determined by a number of factors including cost, availability, processing ease, and inherent barrier properties. Defining an optimal shell material for a given application can be complex since many interacting parameters determine success of a given capsule shell material.

Encapsulated perfume compositions are being used with increasing frequency in a wide variety of consumer products, including household care and personal care products. In the fields of deodorants and antiperspirants, two types of shell material have been employed in commercial applications, according to the applicant's knowledge. Starch core-shell capsules have been employed in commercial deodorant and antiperspirant products for their ability to release perfume when moistened by sweat. Whereas, encapsulated perfume compositions based on gelatin core-shell capsules have also been employed in commercial deodorant and antiperspirant products for their ability to fracture and deliver perfume, in response to mechanical action, e.g. pressing or rubbing against skin or hair or articles of clothing.

Gelatin core-shell capsules are typically formed by a process of complex coacervation. This process is well known in the art and proceeds when gelatin and another colloid in an aqueous external phase of an oil-water emulsion are caused to coacervate and absorb on the surface of oil droplets dispersed in the external phase. A characteristic of this process is that all of the shell-forming materials are contained in a single phase—the external aqueous phase. The shell-forming constituent materials diffuse or migrate through this single phase to reach the oil-water interface and form the shell. Still further, when forming perfume encapsulates in this way, one typically employs as the dispersed phase, droplets of a sacrificial oil or solvent having a very high C log P. The high interfacial tension formed at the oil-water interface promotes the formation of capsule shell with substantially uniform thickness. The blank capsules that are formed can then be immersed in a perfume composition, which diffuses into the capsule cores to displace, or substantially displace, the sacrificial oil or solvent to form an encapsulated perfume composition.

EP 2 221 039 and EP 2 179 719 disclose deodorant and antiperspirant compositions containing encapsulated perfume compositions based on gelatin core-shell capsules. The capsules are characterized by exhibiting a very well defined and regular shell thickness.

Encapsulated perfume compositions based on polyurea core-shell capsules are also known in the art. These capsules are formed by a process of interfacial polymerization. An oil-in-water emulsion is prepared as in the coacervation process described above, but in this process, the shell-forming materials are contained in both the dispersed oil phase and the continuous aqueous phase. Significantly, shell-forming material must diffuse through two different phases in order to reach the oil-water interface before reacting to form the capsule shell. The shell properties or characteristics will be directly affected by the composition of the oil phase, which in the case of a perfume oil, will typically contain tens or even hundreds of different perfume ingredients, each having its own physical and chemical properties (such as solubility and partition coefficient). The rate at which a shell-forming material will be able to diffuse towards the oil-water interface will vary depending on the composition of the complex perfume oil. As a result, shell morphology, in particular shell thickness and uniformity, may be difficult to control precisely.

To-date, applicant is not aware of any commercial applications in which fragrance is delivered from polyurea core-shell capsules.

It is known to employ encapsulated perfume compositions in leave-on personal care products both to fragrance the human or animal body, and to counteract malodour. Leave-on products are those personal care products that adapted for topical application to hair or skin of a subject, and left on the body for a prolonged period of time. Particularly important categories of leave-on products for the modern consumer are deodorants and antiperspirants. Body odour is undesirable and may even be considered unhygienic and anti-social. Body odours emanate as a result of the action of micro-flora on human sweat. Regular bathing to remove sweat can address the build-up of body malodour, but it is not always practical or possible to bath or shower on a frequent basis. Accordingly, the application of deodorants and antiperspirants has become an important aspect of modern body care regimens.

A problem common to encapsulated perfume compositions across all categories of application, including deodorants and antiperspirants, is perfume retention and the prevention of uncontrolled leakage of perfume from the capsules into the surrounding media in which they are dispersed. When encapsulated perfume compositions are placed in consumer products they can suffer from serious stability issues, such as capsule breakage under the effect of osmotic pressure, or extraction of perfume from the capsule under the action of external media. The challenge for the formulator is to create encapsulation technology that must not only exhibit good perfume retention pre-application, it must do this without adversely affecting the ability of the capsule to release perfume when required in application.

Leave-on products (particularly antiperspirants and deodorants) present particular challenges for formulators of encapsulated perfume compositions. Consumers communicate intimately with these products from the moment of application and for many hours thereafter, until the next opportunity to bathe presents itself. A particular problem arises with continual perfume release. This can irritate the consumer and also lead to habituation. Accordingly, particularly in such applications, encapsulated perfume compositions should not be so fragile that the capsules break and release perfume at the slightest frictional contact with the surface of skin, hair or fabric. On the other hand, because sweating results from physical activity, capsules should break and release bursts of perfume in response to frictional forces with skin and/or fabrics, consistent with vigorous physical activity over prolonged periods of time. An 'on-demand' perfume release can provide an olfactive cue for consumers, indicating a product's efficacy, which in turn inspires consumer confidence in a product.

Current perfume encapsulation technology based on starch or gelatin capsules is unable to provide this on-demand release over prolonged periods of time ranging from a period of at least 6 hours up to 10 hours or more, and whereas polyurea capsules represent a promising technology in this regard, heretofore, polyurea capsules have proven difficult to produce with the correct release characteristics in a reliable manner.

There remains a need to provide encapsulated perfume compositions comprising polyurea capsules, particularly useful in leave-on personal care products, and more particularly deodorants and antiperspirants.

More particularly, there remains a need to provide said encapsulated perfume compositions, which are sufficiently stable over time in consumer products, which contain media that are aggressive to encapsulated perfume compositions, such as media containing high levels of salts and surfactants.

Still further, there remains a need to provide said encapsulated perfume compositions possessing the above characteristics, yet which are sufficiently frangible such that when subjected to mechanical forces, consistent with vigorous rubbing against skin or fabrics, will release perfume with sufficient intensity to provide a perception of freshness for a period of at least 6 hours, and up to 10 hours post application.

Applicant has addressed the problems with the prior art and the unmet needs, and provides in a first aspect an encapsulated perfume composition particularly for use in personal care products adapted to be applied to and left on the skin or hair of a human or animal subject, said encapsulated perfume composition comprising one or more polyurea capsules having a volume average capsule diameter of 20 to 90 microns, more particularly 20 to 75 microns, and still more particularly 20 to 50 microns, more particularly still 30 to 50 microns.

As used herein, the volume average particle size is measured by light scattering measurements using a Malvern 2000S instrument and the Mie scattering theory. The principle of the Mie theory and how light scattering can be used to measure capsule size can be found, for example H. C. van de Hulst, Light scattering by small particles. Dover, N.Y., 1981. The primary information provided by static light scattering is the angular dependence of the light scattering intensity, which in turn is linked to the size and shape of the capsules. However, in a standard operation method, the size of a sphere having a size equivalent to the size of the diffracting object, whatever the shape of this object, is calculated by the Malvern proprietary software provided with the apparatus. In case of polydisperse samples, the angular dependence of the overall scattering intensity contains information about the size distribution in the sample. The output is a histogram representing the total volume of capsules belonging to a given size class as a function of the capsule size, whereas an arbitrary number of 50 size classes is typically chosen.

Experimentally, a few drops of slurry containing about 10% of capsules are added to a circulating stream of degased water flowing through a scattering cell. The angular distribution of the scattering intensity is measured and analyzed by Malvern proprietary software to provide the average size and size-distribution of the capsules present in the sample. In the context of the present invention the percentiles Dv 10, Dv 50 and Dv 90 are used as characteristics of the capsule size distribution, whereas Dv 50 corresponds to the median of the distribution.

In a particular embodiment of the present invention, in the encapsulated perfume composition, the shell weight of the polyurea capsules, expressed as a percentage of the total weight of the capsules (shell material+core material), is about 5% to 40%, more particularly 10 to 25% by weight and still more particularly 12% to 20%.

In a particular embodiment of the present invention, the encapsulated perfume composition is provided in the form of a slurry comprising polyurea capsules dispersed in an aqueous dispersing medium.

Shell weight is an important parameter in determining both the stability the performance of the encapsulated perfume composition of the present invention. In particular, the shell weight in relation to the volume average diameter of the capsules determines the release characteristics of the encapsulated perfume composition. More particularly, the stability and performance of the capsules is optimal if the ratio of the shell weight (expressed in % by weight of the total capsule weight: shell material+core material) to the capsule diameter (expressed in microns) is about 0.7 microns$^{-1}$ or less, still more particularly 0.6 microns$^{-1}$ or less, and still more particularly 0.2 microns$^{-1}$ or less.

Having regard to the difficulty of producing polyurea capsules with highly uniform shell thickness, applicant found that shell weight is a reliable parameter for in-process control during capsule formation. By manipulating shell weight (by controlling the amount of shell-forming monomers added during the encapsulation process) and the capsule diameter within the parameters described above, it is possible to produce an encapsulated perfume composition having a desired release profile for the purpose of the invention. More particularly, applicant found that it was possible to obtain capsules that were sufficiently mechanically robust, such that when unactivated (i.e. when they are not subjected to compression or shear forces) they provide very little perfume impression, but which release perfume in response to vigorous mechanical agitation consistent with strenuous physical activity.

This enables the encapsulated perfume composition to be stably incorporated into all manner of consumer products, but particularly leave-on products, such as deodorants and antiperspirants, whilst retaining the capability of being sheared by frictional contact between skin and skin or clothing, when in use.

In a particular embodiment of the present invention, the nominal rupture stress of the polyurea capsules, expressed as MPa, is in the range of about 0.1 to 2 MPa, more particularly 0.2 to 1.5 MPa and still more particularly 0.4 to 1 MPa.

The nominal rupture stress can be measured by the micro-manipulation technique, which is known in the art. The capsules are diluted in distilled water and dried on a microscope stage for about 30 minutes at room temperature (24±1° C.). The principle of the micro-manipulation technique is to compress a single capsule between two parallel surfaces. A single capsule is compressed and held, compressed and released, and compressed to large deformations or rupture at a pre-set speed of 1 micrometer per second. Simultaneously, the force being imposed on them and their deformation can be determined. The technique uses a fine probe positioned perpendicular to the surface of the capsule sample. The probe is connected to a force transducer, which is mounted on a 3-dimensional micro-manipulator that can be programmed to travel at a given speed. The whole process is carried out on an inverted microscope. From the curve of force versus sampling time, the relationship between the force and the capsule deformation to bursting, and its initial diameter are obtained. The technique of micro-manipulation is more fully explained in Zhang, Z., Saunders, R. and Thomas, C. R., Micromanipulation measurements of the bursting strength of single microcapsules, Journal of Microencapsulation 16(1), 117-124 (1999), which document is incorporated herein by reference. The force at capsule rupture expressed in force units (Newton), which is then converted to rupture stress, expressed in pressure units (Pascal), through dividing the rupture force by the cross-sectional area of the capsule. The tip, or probe, used for the micro-manipulation should be approximately the same size as the capsules, and is typically between 10-50 microns. Typically, the force at rupture is measured on single capsules and repeated over typically 50 capsules and the average value is used to calculate the nominal rupture stress according to the present invention.

The capsule cores of the encapsulated perfume compositions contain perfume oil. The perfume oil contains one or more perfume ingredients. In general terms, perfume ingredients will belong to chemical classes as varied as alcohols, ketones, esters, ethers, acetates, terpene hydrocarbons, nitrogenous or *sulphurous* heterocyclic compounds and essential oils, which can be of natural or synthetic origin. Many of these perfume ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery.

As is generally known in the art, both the efficiency with which perfume is encapsulated during capsule formation, as well the reduction of perfume leakage from formed capsules, can be promoted through the use of high amounts of perfume ingredients having a relatively high C log P. Typically, in order to achieve good encapsulation efficiency and low leakage, it is conventional to use at least about 50%, more particularly more than about 60%, and still more particularly more than about 70%, and more particularly still, more than 80% by weight of perfume ingredients having a C log P of about 2.5 or greater, and more particularly 3.3 or greater, and still more particularly 4.0 or greater. Use of such perfume ingredients is generally regarded as helpful in reducing diffusion of perfume through a capsule shell and into a product base under specific time, temperature, and concentration conditions.

The values of C log P of perfume ingredients have been reported in many databases, including the Pomona 92 database, available from Daylight Chemical Information Systems, Inc., Daylight CIS, Irvine, Calif.

It is common to use solvents in admixture with perfume ingredients. Solvent materials are hydrophobic materials that are miscible in perfume ingredients, and which have little or no impact on the quality of the perfume in the quantities employed. Solvents commonly employed have high C log P values, for example greater than 6 and even greater than 10. Solvents include triglyceride oil, mono and diglycerides, mineral oil, silicone oil, diethyl phthalate, polyalphaolefins, castor oil and isopropyl myristate.

US2011071064 is concerned with polyurea capsules for use in personal care applications. It is particularly concerned with means of manipulating the shell properties of capsules in order to manipulate the rate at which they release perfume. It is stated therein, that a solvent should be employed in the core in an amount of greater than 10%, more particularly greater than 30%, and still more particularly greater than 70% by weight.

In contrast with this finding, the applicant surprisingly found that it is possible to employ substantially no solvent material in the core material of polyurea capsules of the present invention. Indeed, applicant found that it is possible to prepare encapsulated perfume compositions wherein the encapsulated cores are composed entirely of perfume ingredients and no solvents.

Solvent-free encapsulated perfume compositions may be employed, in particular, when the perfume ingredients making up the core material have limited water solubility. In particular, the core material should be formed with a large proportion of perfume ingredients having a solubility in water of 15,000 ppm or less, more particularly 5000 ppm or less, and still more particularly 3000 ppm or less. More particularly, at least 60%, more particularly at least 70% and still more particularly at least 80%, and still more particularly greater than 90% of perfume ingredients should have a solubility in water of 15,000 ppm or less, more particularly 5000 ppm or less, and still more particularly 3000 ppm or less.

Avoiding the use of a solvent in the capsule cores is generally advantageous in terms of cost and impact on the environment. But more particularly, in relation to leave-on products, if one is able to prepare capsules with high perfume loading by avoiding the use of solvents, one can prepare encapsulated perfume compositions with lower levels of capsules. Naturally, the lower the concentration of capsules employed, the less likelihood there is of visible residue being deposited on garments that come into intimate contact with treated skin.

The concentration of capsules employed in a slurry required to obtain a desired perfumery effect, will depend to an extent upon how efficiently perfume can be encapsulated, and in turn, this will be influenced by the amount of shell material employed relative to the amount of core material.

In a particular embodiment of the present invention, the capsule loading (encapsulated material+shell material) in the slurry is in the range of about 5% to 75%, more particularly 25% to 50%, and still more particularly 30% to 40% by weight based on the weight of the slurry.

Furthermore, the total amount of perfume ingredients expressed as a percentage by weight based on the weight of the slurry is in the range of about 10% to 50%, more particularly 20% to 40% and still more particularly 25 to 35% by weight.

Further still, these high loadings of perfume ingredients can be encapsulated despite the relatively low shell weight. Indeed, in another aspect of the present invention, the amount of core content expressed as weight percentage based on the total weight of the capsules may range from about 60% to 95% by weight, more particularly 75% to 80% and still more particularly 80% to 88% by weight.

The core-shell weight ratio may be obtained by weighing an amount of capsules that have been previously washed with water and separated by filtration. The core is then extracted by solvent extraction techniques to give a core weight. The shell weight is obtained from simple mass balance taking into account the initial amount of encapsulating materials in weight %.

As stated hereinabove, the encapsulated perfume composition of the present invention may be employed to encapsulate any perfume ingredients. However, there can be difficulties associated with the encapsulation of perfume ingredients possessing aldehyde functionality. More specifically, it is known that perfume ingredients containing aldehyde functionality will react with the amine functionality of monomers used in capsule wall formation. This can result in the complete failure to encapsulate perfumes containing aldehyde perfume ingredients, or if capsules are formed, the loading of perfumes is low, and the capsules are susceptible to aggregation. Low perfume oil retention is costly, whereas aggregation phenomena are at the very least aesthetically undesirable and at worst can lead to manufacturing problems and poor capsule performance, and so should preferably be avoided as much as possible.

WO2011/161265 proposed a solution to this problem, which consisted in presenting aldehyde perfume ingredients in the form of aldehyde precursors, in which the aldehyde functionality is protected and therefore unable to react with amine monomers during capsule formation. Whereas this is an interesting solution to the problem, nevertheless there is additional cost and complexity associated with preparing precursors of aldehyde perfume ingredients.

In a particular embodiment of the present invention, when the encapsulated perfume composition is employed to encapsulate aldehyde-containing perfume ingredients, in addition to said aldehyde perfume ingredients, the encapsulated perfume should contain a non-aromatic cyclic perfume ingredient, and an alkyl salicylate and/or a 2,2,2-trisubstituted acetal, wherein said acetal has the general formula

$$R_1R_2R_3C\text{---}CH(OR_4)(OR_5)$$

wherein $R_1$ is a saturated or unsaturated alkyl or aromatic residue having at least 4 carbon atom, more preferably at least 5 carbon atoms and most preferably at least 6 carbon atoms, but not more than 10 carbon atoms; $R_2$ and $R_3$ are independently selected from a saturated or unsaturated alkyl residue having at least on carbon atom; and $R_4$ and $R_5$ are independently selected from either a methyl group and/or an ethyl group.

In a more particular embodiment of the invention in addition to an aldehyde-containing perfume ingredient, the encapsulated perfume comprises a non-aromatic cyclic perfume ingredient and an alkyl salicylate.

In a more particular embodiment of the invention the encapsulated perfume comprises a non-aromatic cyclic perfume ingredient and an alkyl salicylate and a 2,2,2-trisubstituted acetal, hereinabove defined.

The term "cyclic perfume ingredient" as used herein refers to a molecule useful as a perfume ingredient, which contains within its chemical structure a series of atoms that forms a closed ring. That ring may be aromatic or aliphatic. It may be mono- or poly-cyclic, and it may contain heteroatoms. The ring may bear substituents or it may be unsubstituted.

The aldehyde perfume ingredient may be any aldehyde useful in perfumery or as a flavourant. The skilled person in the art of perfumery has available to it a palette of ingredients containing aldehyde functionality, and these ingredients are contemplated in the present invention as representing aldehyde perfume ingredients. The aldehyde may be an aliphatic aldehyde, a cycloaliphatic aldehyde, and acyclic terpene aldehyde, a cyclic terpene aldehyde, or an aromatic aldehyde.

More particularly, the aldehydes include, but are not limited to, the following group of aldehydes, wherein the CAS numbers are provided in parentheses. Herein, where trivial or non-systematic names are employed for fragrance ingredients, the skilled person will understand that these names and CAS numbers are intended to also include synonyms based on more formal systems of nomenclature, such as IUPAC:

DECANAL (112-31-2), 2-METHYL DECANAL (ALDEHYDE C-11 (19009-56-4), 10-UNDECEN-1-AL (112-45-8), UNDECANAL (112-44-7), DODECANAL (112-54-9), 2-METHYL UNDECANAL (110-41-8), HEPTANAL (111-71-7), OCTANAL (124-13-0), GREEN HEXANAL (5435-64-3), NONANAL (124-19-6), UNDECENAL MIXTURE (1337-83-3), (Z)-4-DECENAL (21662-09-9), (E)-4-DECENAL (65405-70-1), 9-DECENAL (39770-05-3), ISOVALERIANIC ALDEHYDE (590-86-3), AMYL CINNAMIC ALDEHYDE 122-40-7), METHYL CINNAMIC ALDEHYDE (101-39-3), METHYL PHENYL HEXENAL (21834-92-4), PHENYL PROPIONIC ALDEHYDE (104-53-0), PARA TOLYL ALDEHYDE (104-87-0), PARA ANISALDEHYDE (123-11-5), BENZALDEHYDE (100-52-7), CYCLAL C (68039-49-6), TRICYCLAL (68039-49-6), CYCLOMYRAL (68738-94-3), ISOCYCLOCITRAL (1335-66-6), MACEAL (68259-31-4), SAFRANAL (116-26-7), HELIOTROPINE (120-57-0), HEXYL CINNAMIC ALDEHYDE (101-86-0), BOURGEONAL (18127-01-0), CINNAMIC ALDEHYDE (104-55-2), CUMINIC ALDEHYDE (122-03-2), CYCLAMEN ALDEHYDE (103-95-7), CYCLOHEXAL (31906-04-4), FENNALDEHYDE (5462-06-6), FLORALOZONE (67634-15-5), FLORHYDRAL (125109-85-5), HYDRATROPIC ALDEHYDE (93-53-8), LILIAL (80-54-6), MEFRANAL (55066-49-4), MYRALDENE (37677-14-8), SILVIAL (6658-48-6), TRIFERNAL (16251-77-7), 2-TRIDECENAL (7774-82-5), DUPICAL (30168-23-1), SCENTENAL (86803-90-9), PRECYCLEMONE B (52475-86-2), VERNALDEHYDE (66327-54-6), HEXANAL (66-25-1), ADOXAL (141-13-9), CALYPSONE (929253-05-4), CETONAL (65405-84-7), CITRAL (5392-40-5), CITRONELLAL (106-23-0), CITRONELLYL OXYACETALDEHYDE (7492-67-3), DIHYDRO FARNESAL (32480-08-3), HYDROXYCITRONELLAL (107-75-5), MELONAL (106-72-9), METHOXYMELONAL (62439-41-2), NONADIENAL (557-48-2), ONCIDAL (54082-68-7), PINOACETALDEHYDE (33885-51-7), TETRAHYDRO CITRAL (5988-91-0), TROPIONAL (1205-17-0), ETHYL VANILLIN (121-32-4), VANILLIN (121-33-5).

When assigning perfume ingredients to categories, a perfume ingredient that contains both aldehyde functionality and a ring, is consider to be an aldehyde perfume ingredient for the purpose of the present invention, and not a cyclic perfume ingredient.

The extent or severity of any observed aggregation phenomenon depends on a number of factors, including the reactivity of the aldehyde perfume ingredient towards monomers (e.g. amine monomers) used in forming the capsule shells, as well as the solubility of the aldehyde perfume ingredient in aqueous media. As the capsule shell-forming process is an interfacial process and the amines used are substantially contained in the aqueous phase, the extent to which an aldehyde perfume ingredient will partition into the aqueous phase, may also affect its reactivity towards the amine.

In a particular embodiment of the present invention, the encapsulated perfume composition may contain up to about 6% by weight of aldehyde perfume ingredients based on the total weight of the encapsulated perfume. More particularly, the encapsulated perfume composition contains encapsulated aldehyde perfume ingredients within the range of 0.01% to 6% by weight, more particularly still 0.01 to 5.5%, still more particularly 0.01 to 5%, still more particularly 0.01 to 4.5%, still more particularly 0.01 to 4.0%, still more particularly 0.01 to 3.5%, still more particularly 0.01 to 3%, still more particularly 0.01 to 2%, still more particularly 0.01 to 1% by weight.

Non-aromatic cyclic perfume ingredients include, but are not limited to, cyclic esters, ketones, ketals and alcohols. Particularly useful non-aromatic cyclic perfume ingredients in the present invention are cyclic esters. Examples of useful cyclic esters include ACETYLATED CLOVE OIL TERPENES (68425-19-4), AGRUMEX (88-41-5), ALLYL CYCLOHEXYL PROPIONATE (2705-87-5), AMBER CORE (139504-68-0), AMBREINE (8016-26-0), AMBREINOL (73138-66-6), AMBRETTOLIDE (28645-51-4), AMBRINOL (41199-19-3), AMBROFIX (6790-58-5), APHERMATE (25225-08-5), AZARBRE (68845-36-3), BICYCLO NONALACTONE (4430-31-3), BOISIRIS (68845-00-1), BORNEOL (507-70-0), BORNYL ACETATE LIQUID (125-12-2), PARA BUTYL CYCLOHEXANOL (98-52-2), PARA BUTYL CYCLOHEXYL ACETATE (32210-23-4), CAMONAL (166301-22-0), CAMPHOR SYNTHETIC (76-22-2), LAEVO CARVONE (6485-40-1), CASHMERAN (33704-61-9), CEDRENE (11028-42-5), CEDRENOL (28231-03-0), CEDROL (77-53-2), WOODY EPDXIDE (71735-79-0), CEDRYL ACETATE CRYSTALS (77-54-3), CEDRYL METHYL ETHER (19870-74-7), CELERY KETONE (3720-16-9), CETALOX (3738-00-9), CIVETTONE (542-46-1), CONIFERAN (67874-72-0), CORANOL (83926-73-2), COSMONE (259854-70-1), CYCLOGALBANATE (68901-15-5), CYCLOHEXYL ETHYL ACETATE (21722-83-8), CYPRISATE (23250-42-2), DAMASCENONE (23696-85-7), ALPHA DAMASCONE (24720-09-0), BETA DAMASCONE (23726-92-3), DELTA DAMASCONE (57378-68-4), DELTA DECALACTONE (705-86-2), GAMMA DECALACTONE (706-14-9), DECATONE (34131-98-1), DIHYDRO AMBRATE (37172-02-4), BETA DIHYDRO IONONE (17283-81-7), DIHYDRO JASMONE (1128-08-1), DELTA DODECALACTONE (713-95-1), DODECALACTONE GAMMA (2305-05-7), DUPICAL (30168-23-1), ETHYL SAFRANATE (35044-59-8), ETHYLENE BRASSYLATE (105-95-3), EUCALYPTOL (470-82-6), ALPHA FENCHONE (7787-20-4), FENCHYL ACETATE (13851-11-1), FENCHYL ALCOHOL (1632-73-1), FLOROCYCLENE (68912-13-0), FLOROSA (63500-71-0), FLORYMOSS (681433-04-5), FOLENOX (26619-69-2), FOLROSIA (4621-04-9), FRESKOMENTHE (14765-30-1), FRUITATE (80623-07-0), GALBANONE PURE (56973-85-4), GARDOCYCLENE (67634-20-2), GEORGYWOOD (185429-83-8), GIVESCONE (57934-97-1), GLYCOLIERRAL (68901-32-6), GRISALVA (68611-23-4), GYRANE (24237-00-1), HABANOLIDE (111879-80-2), HEDIONE (24851-98-7), HEPTALACTONE GAMMA (105-21-5), HERBANATE (116126-82-0), HERBAVERT (67583-77-1), HERBOXANE (54546-26-8), BETA IONONE (8013-90-9), IRISANTHEME (1335-46-2), ALPHA IRISONE (8013-90-9), ALPHA IRONE (79-69-6), IRONE F (54992-91-5), ISO E SUPER (54464-57-2), ISOJASMONE B 11 (95-41-0), ISOLONGIFOLANONE (23787-90-8), ISOMENTHONE DL (491-07-6), ISOPULEGOL (89-79-2), ISORALDEINE 40, 70 and 90 (1335-46-2), JASMACYCLENE (5413-60-5), JASMATONE (13074-65-2), JASMOLACTONE (32764-98-0), CIS JASMONE (488-10-8), JASMONYL (18871-14-2), KARANAL (117933-89-8), KEPHALIS (36306-87-3), LAITONE (4625-90-5), LIGANTRAAL (68738-99-8), MAYOL (13828-37-0), MENTHONE (89-80-5), METAMBRATE (72183-75-6), METHYL CEDRYL KETONE (32388-55-9), GAMMA METHYL DECALACTONE (7011-83-8), METHYL DIHYDRO ISOJASMONATE (37172-53-5), METHYL EPI JASMONATE (39924-52-2), METHYL TUBERATE (33673-62-0), MUSCENONE (82356-51-2), MUSCONE (541-91-3), ETHYLENE DODECANOATE (54982-83-1), MUSK LACTONE (3391-83-1), MYRALDYL ACETATE (72403-67-9), NECTARYL (95962-14-4), NIMBEROL (70788-30-6), NIRVANOLIDE (329925-33-9), NOOTKATONE (4674-50-4), NOPYL ACETATE (128-51-8), DELTA OCTALACTONE (698-76-0), GAMMA OCTALACTONE (104-50-7), OKOUMAL (131812-67-4), OPALAL (62406-73-9), ORIVONE (16587-71-6), OXYOCTALINE FORMATE (65405-72-3), PIVACYCLENE (68039-44-1), PLICATONE (41724-19-0), POIRENATE (2511-00-4), QUINTONE (4819-67-4), RHUBOFIX (41816-03-9), RHUBOFLOR (93939-86-7), ROSE OXIDE CO (16409-43-1), ROSE OXIDE LAEVO (3033-23-6), ROSSITOL (215231-33-7), SAFRALEINE (54440-17-4), SANDELA (66068-84-6), SPIRAMBRENE (121251-67-0), SPIROGALBANONE (224031-70-3), SUPERFIX (3910-35-8), THIBETOLIDE (106-02-5), TIMBEROL (70788-30-6), TRIMOFIX O (144020-22-4), DELTA UNDECALACTONE (710-04-3), GAMMA VALEROLACTONE (108-29-2), VELOUTONE (65443-14-3), VELVIONE (37609-25-9), VERDALIA (27135-90-6), VERDOL (13491-79-7), VERTOFIX COEUR (32388-55-9), VETIKOL ACETATE (68083-58-9), VETIVERYL ACETATE (68917-34-0), VETYNAL (57082-24-3).

Useful alkyl salicylates include AMYL SALICYLATE (2050-08-0), ETHYL SALICYLATE (118-61-6), HEXENYL-3-CIS SALICYLATE (65405-77-8), HEXYL SALICYLATE (6259-76-3), ISOBUTYL SALICYLATE (87-19-4), ISOBUTYL SALICYLATE (87-19-4), KARMAFLOR (873888-84-7), METHYL SALICYLATE (119-36-8).

Useful 2,2,2-substituted acetals include METHYL PAMPLEMOUSSE (67674-46-8), AMAROCIT B (72727-59-4), NEROLIACETAL (99509-41-8).

The non-aromatic cyclic perfume ingredients and alkyl salicylates, independently of each other may be present in amounts of about 10% or greater by weight based on the total weight of encapsulated perfume, more particularly 15% or greater, more particularly 20% or greater, more particularly 25% or greater, still more particularly 30% or greater, more particularly 33% or greater, for example 20 to 99.99%, or 25 to 99.99%, or 25 to 99.99%, or 30 to 99.99%, or 33 to 99.99%.

In a particular embodiment of the present invention the aldehyde perfume ingredients are present in an amount of about 1% to 6% by weight, more particularly 2% to 5.5% by weight, still more particularly 3% to 5% by weight; and the non-aromatic cyclic perfume ingredients and/or alkyl salicylates perfume ingredients are independently present in amounts of more than 30% by weight, still more particularly more than 33% by weight.

In another particular embodiment of the present invention the aldehyde perfume ingredients are present in an amount of about 1% to 6% by weight, more particularly 2% to 5.5% by weight, still more particularly 3% to 5% by weight; the non-aromatic cyclic perfume ingredients and/or alkyl salicylates perfume ingredients independently are present in amounts between 10% and 33% by weight.

In yet another particular embodiment of the invention the aldehyde perfume ingredients are present in an amount of about 1% to 6% by weight, more particularly 2% to 5.5% by weight, still more particularly 3% to 5% by weight; the non-aromatic cyclic perfume ingredients and alkyl salicylates perfume ingredients independently are present in amounts between 10% and 33% by weight and the 2,2,2-substituted acetals are present in amounts of more than 25% by weight, more particularly more than 30% by weight, still more particularly more than 33% by weight.

The encapsulated perfume composition according to the present invention may be prepared by any method known in the art for producing capsules by interfacial polyaddition of an amine with an isocyanate.

Representative preparative methods are disclosed in WO 2011/161229 and WO 2011/160733. According to WO 2011/161229 or WO 2011/160733 the polyurea microcapsules are prepared in presence of polyvinylpyrrolidone (PVP) as a protective colloid.

WO 2012/107323 discloses polyurea microcapsules having a polyurea shell comprising the reaction product of a polyisocyanate with guanazole and an amino acid in presence of anionic stabilizers or surfactants like anionic polyvinyl alcohol, such as Mowiol® KL-506 sold by Kuraray.

EP-B-0 537 467 describes microcapsules prepared from isocyanates which are containing polyethylenoxide groups, in the presence of stabilizers like polyvinyl alcohol, e.g. partially or totally saponified polyvinyl acetate.

WO 2007/096592 described a microencapsulation process in which an oil phase is emulsified in a continuous aqueous phase, generally stabilized by a surfactant system like polyvinyl alcohols or carboxylated and sulphonated derivatives thereof.

In a typical preparatory method, an encapsulated perfume composition can be prepared according to a procedure in which an aqueous phase is prepared containing a surfactant and/or a protective colloid such as those described below. The aqueous phase is stirred vigorously for a time period of only a few seconds up to a few minutes. A hydrophobic phase may then be added to the aqueous phase. The hydrophobic phase will contain perfume to be encapsulated, and an isocyanate. The hydrophobic phase may also include suitable solvents, although, in a preferred aspect of the present invention, no solvents are employed. After a period of vigorous stirring, an emulsion is obtained, in which the hydrophobic phase is dispersed as tiny droplets in the aqueous continuous phase. The rate of stirring may be adjusted to influence the size of droplets of hydrophobic phase in the aqueous phase.

An aqueous solution containing the amine is then added to initiate the polyaddition reaction. The amount of amine which is introduced is usually in excess, relative to the stoichiometric amount needed to convert the free isocyanate groups.

The polyaddition reaction proceeds generally at a temperature ranging from approximately 0 to 100 degrees centigrade, for a period of time ranging from a few minutes to several hours.

Conditions for creating capsules by interfacial polyaddition are well known in the art and no further elaboration of those conditions, which are within the purview of the skilled person, is needed here. Specific description relating to the preparation of the capsules is provided in the examples below.

Amines useful in the formation of capsules include those compounds containing one or more primary or secondary amine groups, which can react with isocyanates to form polyurea. When the amine contains only one amino group, the compound will contain one or more additional functional groups that would form a network through a polymerisation reaction.

Examples of suitable amines include 1,2-ethylenediamine, 1,3-diaminopropane, 1,4-diaminobutane, 1,6-diaminohexane, hydrazine, 1,4-diaminocyciohexane and 1,3-diamino-1-methylpropane, diethylenetriamine, triethylenetetramine and bis(2-methylaminoethyl) methylamine.

Other useful amines include poly ethyieneamine (CH2CH2NH)n such as etheyleneamine, diethyleneamine, ethylene diamine, triethylenetetramine, tetraethylenepentamine; poly vinylamine (CH2CHNH2)n sold by BASF (Lupamine different grades); poly ethyleneimine (CH2CH2N)x-(CH2CH2NH)y-(CH2CH2NH2)z sold by BASF under Lupasol™ grades; poly etheramine (Jeffamine from Huntsman); guanidine, guanidine salt, melamine, hydrazine and urea.

A particularly preferred amine is a polyethyleneimine (PEI), more particularly a PEI from the Lupasol™ range supplied by BASF, still more particularly Lupasol™ PR8515.

Isocyanates useful in the formation of polyurea microcapsules include di- and tri-functionalised isocyanates such as 1,6-diisocyanatohexane, 1,5-diisocyanato-2-methylpentane, 1,5-diisocyanato-3-methylpentane, 1,4-diisocyanato-2,3-dimethylbutane, 2-ethyl-1,4-diisocyanatobutane, 1,5-diisocyanatopentane, 1,4-diisocyanatobutane, 1,3-diisocyanatopropane, 1,10-diisocyanatodecane, 1,2-diisocyanatocyclobutane, bis(4-isocyanatocyclohexyl)methane, or 3,3,5-trimethyl-5-isocyanatomethyl-1-isocyanatocyclohexane.

Other useful isocyanates include also the oligomers based on those isocyanate monomers, such as homopolymer of 1,6-diisocyanatohexane. All those monomers and oligomers are sold under the trade name Desmodur by Bayer. Also included are the modified isocyanates and in particular, the waterdispersible isocyanate such as Hydrophilic Aliphatic Polyisocyanate based on Hexamethylene Diisocyanate, (sold under the name BAYHYDUR™).

The classes of protective colloid or emulsifier, which may be employed include maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide, ethylenediamine and ethylene oxide, polyvinylpyrrolidone, polyvinyl alcohols, fatty acid esters of polyoxyethylenated sorbitol and sodium dodecylsulfate.

Particular protective colloids include polyvinyl alcohol copolymers having a degree of hydrolysis in the range of 85 to 99.9%. As used herein, the term "polyvinyl alcohol copolymer" means a polymer of vinyl alcohol/vinyl acetate with comonomers.

It is known that polyvinyl alcohol is produced by hydrolysis (deacetylation) of polyvinyl acetate, whereby ester groups of polyvinyl acetate are hydrolysed into hydroxyl groups, thus forming polyvinyl alcohol.

The degree of hydrolysis reflects the percentage of groups that are converted by hydrolysis. The term "polyvinyl alcohol" qualified by a degree of hydrolysis, means therefore, a vinyl polymer containing both ester and hydroxyl groups.

In a particular embodiment of the invention, copolymers of polyvinyl alcohol with a degree of hydrolysis in the range of 85 to 99.9%, more particularly 85 to 95% may be used as protective colloids.

The degree of hydrolysis can be determined by techniques well known in the art, for example, according to DIN 53401.

The polyvinyl alcohol copolymers contain addition co-monomers, that is, co-monomers that are polymerized with a vinyl ester in a first step, followed by hydrolysis of the ester groups to form the copolymer of polyvinyl alcohol in a second step. Copolymers may be formed by radical polymerization of vinyl acetate and co-monomers in a manner known per se.

Polyvinyl alcohol copolymers may contain unsaturated hydrocarbons as co-monomers. These hydrocarbons may be modified with charged or non-charged functional groups. Particular co-monomers include, but are not limited to:—
  unsaturated hydrocarbons with 2 or 3 carbon atoms and no functional groups, e.g. ethylene;
  unsaturated hydrocarbons having 2 to 6 carbon atoms and non-charged functional groups, such as hydroxyl groups, e.g. buten-1,4-diol;
  unsaturated hydrocarbons having anionic groups, such as carboxyl, and/or sulphonic acid groups;
  unsaturated hydrocarbons having cationic groups, such as quaternary ammonium groups.

Particular copolymers of polyvinyl alcohol include those having a degree of hydrolysis of 85 to 99.9%, and more particularly 85 to 95%; and which contain:—
  0.1 to 30 mol % of co-monomers containing anionic groups as mentioned above; or
  0.1 to 30 mol % of co-monomers containing cationic groups as mentioned above; or
  0.1 to 30 mol % of co-monomers with unsaturated hydrocarbons having 2 to 6 carbon atoms and non-charged functional groups, especially two hydroxyl groups, wherein mol % is based on the vinyl acetate/co-monomer polymerization mixture.

Suitable copolymers of polyvinyl alcohol and co-monomers having 1,2 diol structure are described in EP 2 426 172 and EP 2 648 211, which are herein incorporated by reference.

The following protective colloids are particularly useful in the preparation of polyurea capsule compositions of the present invention:—
  Anionic polyvinyl alcohol copolymers with a degree of hydrolysis of greater than 80%, preferably 85.0% to 995%, and a viscosity of 2 mPas to 70 mPas (DP 100-6000), for example K-polymer KL-318 from Kuraray (viscosity 20-30 mPas, hydrolysis 85.0 to 90.0%); Gohsenal T-350 from Nippon Gohesi (viscosity 27-33 mPas, hydrolysis 93.0 to 95.0%); Gohseran L-3266 from Nippon Gohsei (viscosity 2.3 to 2.7 mPas, hydrolysis 86.5 to 89.0%)
  Non-charged polyvinyl alcohol copolymers with a degree of hydrolysis of greater that 80%, preferably 85.0 to 99.5%, and a viscosity of 2 mPas to 70 mPas (DP 100-6000), for example G-polymer OKS-8041 from Nippon Gohsei (viscosity 2.8 to 3.3 mPas, hydrolysis 88.0 to 90.0%), G-polymer AZF-8035 from Nippon Gohsei (viscosity 2.8 to 3.3 mPas, hydrolysis 98.5 to 99.5%); and
  Cationic polyvinyl alcohol copolymers with a degree of hydrolysis of greater than 80%, and more particularly 85.0 to 99.5%, and a viscosity of 2 mPas to 70 mPas (DP 100-6000), for example Gohsefimer K-210 from Nippon Gohsei (viscosity 18.0 to 22.0 mPas, hydrolysis 85.5 to 88.0%).

The protective colloid may or may not be a constituent of the capsule shell. Generally, the total amount of protective colloid expressed as a percentage by weight based on the weight of the slurry is in the range of about 0.1 to 20%, more particularly 1% to 10% and still more particularly 1.5% to 5% by weight.

Combinations of two or more different protective colloids may also be employed in the present invention.

If the encapsulated perfume composition is intended to be stored as a slurry, or further incorporated into a consumer product as a slurry, the pH of the slurry is adjusted to a level of about 5 to 10. This may be achieved with the addition of a suitable acid to an alkaline slurry, such as citric acid or formic acid, and a preservative added.

Encapsulated perfume compositions of the present invention can be prepared in the form of an aqueous slurry. However, a problem that can arise with the production of slurries is that the perfume-containing capsules can phase-separate from the aqueous dispersing medium and cream, sediment, or coagulate. In order to properly disperse and suspend capsules within an aqueous dispersing medium, stably over time, dispersing aids are commonly employed in the slurries.

A wide variety of dispersing aids are known in the art, and include polysaccharides, pectine, alginate, arabinogalactan, carageenan, gellan gum, xanthan gum, guar gum, acrylates/acrylic polymers, starches, water-swellable clays, acrylate/aminoacrylate copolymers, and mixtures thereof, maltodextrin; natural gums such as alginate esters; gelatine, protein hydrolysates and their quaternized forms; synthetic polymers and copolymers, such as poly(vinyl pyrrolidone-co-vinyl acetate), poly(vinyl alcohol-co-vinyl acetate), poly (maleic acid), poly(alkyleneoxide), poly(vinylmethylether), poly(vinylether-co-maleic anhydride), and the like, as well as poly-(ethyleneimine), poly((meth)acrylamide), poly (alkyleneoxide-co-dimethylsiloxane), poly(amino dimethylsiloxane), and the like.

Despite the variety of dispersing aids that are available for use, the selection of the appropriate aid, will depend on a number of factors, including the capsule shell chemistry, its morphology, its size and density, as well as composition of the aqueous dispersing media, such as its pH and electrolyte content, which will be determined to a certain extent by the encapsulation process conditions.

Indeed, applicant found it difficult to prepare slurries containing polyurea capsules in a reliably reproducible way. Phase separation, as well as slurry viscosity was difficult to control. When slurry viscosity is too high, high shear forces are needed to process slurry can damage the capsules. Furthermore, viscous slurries can be difficult to handle and can lead to mixing issues when incorporating the encapsulated perfume compositions into consumer product bases.

The applicant has now found, during the course of research leading to the present invention that by employing hydroxyethylcellulose as a dispersing aid, it was possible to form, in a straightforward manner, an encapsulated perfume composition, as a slurry, in which polyurea capsules were stably dispersed, and which possessed an acceptable viscosity.

Therefore, the invention provides in another aspect of the invention an encapsulated perfume composition, as hereinabove described, wherein the capsules are in the form of a stable suspension having a viscosity of up to 3000 centipoise, and more particularly about 150 to 3000 centipoise when measured on rheometer, for example a RheoStress™ 1 instrument (ThermoScientific), using rotating disks at a shear rate of 21 $s^{-1}$ at a temperature of 25° C.

As used hereinabove, the term "stable suspension" is intended to mean a suspension of the polyurea capsules, which upon visible inspection, shows no sign of phase separation, such as creaming, settling, precipitation or coagulation when stored for a period of 2 weeks at a temperature of 50° C.

Any hydroxyethylcellulose that is suitable for use in consumer products may be employed as a dispersing aid in accordance with the present invention. Preferred grades, however, are those suitable for use in cosmetics. Particularly preferred grades include those Natrosol™ products known in the art, and particularly Natrosol™ 250 HX.

In a particular embodiment of the invention, the amount of hydroxyethylcellulose employed in a slurry is about 0.05 to about 1.0%, more particularly 0.05 to 0.5% by weight based on the total weight of the slurry.

Provided hydroxyethylcellulose is employed as a dispersing aid, additional dispersing aids may also be employed. Examples of suitable additional dispersing aids include any of those mentioned herein above. In particular, said additional dispersing aids include starches, such as National 465, Purity W, or starch B990; or acrylate polymer or copolymers such as Tinovis CD, Ultragel 300 and Rheocare TTA.

When additional dispersing aids are employed, they may be used in amounts in the range of about 0.1 to about 5.0%, more particularly 0.5 to 4% by weight and still more particularly 1 to 3% by weight, based on the weight of the slurry.

The hydroxyethylcellulose is preferably added to the slurry once it is formed. Adding hydroxyethylcellulose during the formation of the capsules is preferably avoided because it may increase the viscosity and be detrimental to capsule formation.

In order to prevent microbial contamination the encapsulated perfume composition of the present invention may contain a preservative. The preservative may be encapsulated and/or it may be contained in the aqueous suspending medium of the slurry. Suitable preservatives include quaternary compounds, biguanide compounds, and mixtures thereof. Non-limiting examples of quaternary compounds include benzalkonium chlorides and/or substituted benzalkonium chlorides such as commercially available Barquat® (available from Lonza), Maquat® (available from Mason), Variquat® (available from Witco/Sherex), and Hyamine® (available from Lonza); di(C6-C14)alkyl di short chain (C1-4 alkyl and/or hydroxyalkl) quaternary such as Bardac® products of Lonza; N-(3-chloroallyl) hexaminium chlorides such as Dowicide® and Dowicil® available from Dow; benzethonium chloride such as Hyamine® from Rohm & Haas; methylbenzethonium chloride represented by Hyamine® 10* supplied by Rohm & Haas, cetylpyridinium chloride such as Cepacol chloride available from of Merrell Labs; and diester quaternary ammonium compounds. Examples of preferred dialkyl quaternary compounds are di(C8-C12)dialkyl dimethyl ammonium chloride, such as didecyldimethylammonium chloride (Bardac® 22), and dioctyldimethylammonium chloride (Bardac® 2050). The quaternary compounds useful as cationic preservatives and/or antimicrobial agents herein are preferably selected from the group consisting of dialkyldimethylammonium chlorides, alkyldimethylbenzylammonium chlorides, dialkylmethylbenzylammonium chlorides, and mixtures thereof. Other preferred cationic antimicrobial actives useful herein include diisobutylphenoxyethoxyethyl dimethylbenzylammonium chloride (commercially available under the trade name Hyamine® 1622 from Rohm & Haas) and (methyl)diisobutylphenoxyethoxyethyl dimethylbenzylammonium chloride (i.e. methylbenzethonium chloride).

The encapsulated perfume composition may contain surfactants. Surfactants include non-ionic, cationic, anionic and zwitterionic varieties.

In addition to encapsulated perfume, the slurry may contain non-encapsulated, i.e. free perfume, external of the capsules in the aqueous carrier medium.

If desired the encapsulated perfume composition as herein described, in the form of a slurry, may be dehydrated to provide an encapsulated perfume composition in powder form, which represents another aspect of the invention.

The slurry may be dried using techniques known in the art. For example, it may be dried by decanting off the liquid from the suspension and drying the capsules in an oven to produce a cake, which can then be rendered in powder form by a subsequent comminution step.

Preferably, however, drying of the slurry is carried out by spray drying or fluid-bed drying without further handling.

Spray drying techniques and apparatus are well known in the art. A spray-drying process pushes suspended capsules through a nozzle and into a drying chamber. The capsules may be entrained in a fluid (such as air) that moves inside of a drying chamber. The fluid (which may be heated, for example at a temperature of 150 and 120° C., more preferably between 170° C. and 200° C., and still more preferably between 175° C. and 185° C.) causes the liquid to evaporate, leaving behind the dried capsules, which can then be collected from the process equipment, and further processed.

It is conventional to mix spray dried capsules with flow aids to produce flowable powders that are not susceptible to caking. Flow aids include silicas or silicates, such as precipitated, fumed or colloidal silicas; starches; calcium carbonate; sodium sulphate; modified cellulose; zeolites; or other inorganic particulates known in the art.

It is quite common, given the high temperatures and impaction forces encountered during a spray drying procedure, for core shell capsules to lose some of their core material. Furthermore, it may not be possible to work at sufficiently high temperatures for a sufficiently long period of time to drive off all moisture from the slurry, without compromising the thermal stability of the capsules. Accordingly, the polyurea capsules emerging from a spray-drying process as herein described, may contain small amounts of surface oil, as well as residual moisture. Applicant found, however, that the conventional use of flow aids, added to the dried capsules, was not completely effective to produce the polyurea capsules of the present invention in a free-flowing form that was not prone to caking.

Surprisingly, however, applicant found that if the flow aid was added to the slurry before the spray-drying step, the resultant polyurea capsules produced fine, free-flowing powders that did not cake or show any visible signs of agglomeration.

More particularly, the applicant found that particularly good powders were formed that were free-flowing, resistant to caking, and had low levels of residual moisture and surface oil, when the flow-aid added to the slurry was a form of silica having a volume average particle size that was micron-sized, and more particularly from 1 to about 8 microns, still more particularly from 1 to 7, more particularly from 1 to 6, and still more particularly from 1 to 5 microns.

Still further, the applicant found that employing said silica having a bulk density of about 5 to about 30 lbs/ft$^3$ resulted in particularly good powders that were free-flowing, resistant to caking, and had low levels of residual moisture and surface oil.

Syloid FP grade silicas were particularly preferred flow aids, for example Syloid FP 244, Syloid FP 72, or Syloid FP 63.

Accordingly, the invention provides in another of its aspects a method of making an encapsulated perfume composition as herein defined, in the form of a powder, comprising the step of spray-drying a slurry comprising a plurality of polyurea capsules as herein defined, dispersed in an aqueous medium comprising a silica flow aid as herein above defined.

In another aspect of the present invention there is provided an encapsulated perfume composition as herein defined, in the form of a powder comprising a flow aid as hereinabove described, said powder having a residual moisture content of about 0.1 to about 8% by weight, more particularly 0.5% to 5% and still more particularly 1 to 3% by weight, based on the weight of the slurry.

In yet another aspect of the present invention there is provided an encapsulated perfume composition as herein defined, in the form of a powder comprising a flow aid as hereinabove described, said powder having a surface oil (oil lost from the core) content of less than 5%, more particularly less than 2% and still more particularly less than 0.5% by weight, based on the weight of the powder.

Residual moisture can be measured using the Karl Fisher method, whereas the amount of surface oil can be measured by extracting the powder with a solvent for the oil, and analysing using GC MS.

The present invention also relates to the incorporation of an encapsulated perfume composition as hereinabove defined into a leave-on personal care product. The present invention also relates to a leave-on personal care product containing an encapsulated perfume composition as hereinabove defined.

The encapsulated perfume composition according to the present invention may be incorporated into said products in the form of a slurry or a powder. The amount of encapsulated perfume composition incorporated into said products may range from 0.01% to 25%, more particularly 0.1% to 10% and still more particularly 0.5% to 5% by weight of the finished product.

The encapsulated perfume compositions of the present invention contain polyurea capsules that are shear sensitive, and which are adapted to release its perfume contents by rubbing skin on skin or skin on an article of clothing.

The encapsulated perfume composition of the present invention may be the sole source of perfume material incorporated into said products. However, additional perfume may also be incorporated into said products in the form of free (un-encapsulated) perfume, or other types of encapsulated perfume compositions may be employed with the encapsulated perfume composition of the present invention. Other types of encapsulated perfume compositions may include any capsules known to contain perfume, such as gelatin capsules, starch capsules, acrylic capsules, aminoplast capsules, and the like. The other capsule types may release their perfume by diffusion, or by any external physical stimulus, such as heat, moisture, light, or by abrasion.

The leave-on products include colognes, after-shave lotions, after-bath preparations, splash lotions, moisturizing creams, hair cream, talcum powder and especially deodorant and antiperspirant products.

Deodorants and antiperspirants may take the form of a solid, cream or liquid. These forms are delivered to the body via a variety of devices such as, canisters with elevating devices which hold a free standing solid product (sticks), aerosol sprays, pump sprays, and liquid applicators.

In yet another aspect of the invention there is provided a method to confer, enhance, improve or modify the olfactive properties of a leave-on product, which method comprises incorporating into said product an encapsulated perfume composition as hereinabove defined.

The provision of leave-on products, in particular, deodorant and antiperspirant products, containing an encapsulated perfume composition as hereinabove defined, which reliably releases perfume when subjected to shear forces, such as the frictional force of skin against human or animal skin or skin against an inanimate surface such as a textile, and does so over a period of time up to 6 hours, and more preferably up to 10 hours, addresses an unmet need.

As stated hereinabove, the encapsulated perfume composition of the present invention is particularly suitable for incorporation into leave-on products, and more particularly deodorant or antiperspirant products, and leave-one products containing said encapsulated perfume composition for additional aspects of the present invention. The anti-perspirant and/or deodorant personal care products contain, in addition to the encapsulated perfume composition, at least one deodorant active principle and/or at least one anti-perspirant salt or complex.

Within the meaning of the instant invention, "deodorant active principle" is understood to mean any substance capable of masking, absorbing, improving or reducing the unpleasant odour resulting from the decomposition of human sweat by bacteria.

More specifically, the deodorant active principles can be bacteriostatic agents or bactericidal agents, such as 2,4,4'-trichloro-2'-hydroxydiphenyl ether (® Triclosan), 2,4-dichloro-2'-hydroxydiphenyl ether, 3',4',5'-trichlorosalicylanilide, 1-(3',4'-dichloro-phenyl)-3-(4'-chlorophenyl)urea (®Triclocarban) or 3,7,11-trimethyldodeca-2,5,10-trienol Farnesol); quaternary ammonium salts, such as cetyltrimethyl-ammonium salts or cetylpyridinium salts, DPTA (1,3-diaminopropanetetraacetic acid) or 1,2-decanediol (Simclariol from Symrise).

Mention may also be made, among the deodorant active principles of zinc salts, such as zinc salicylate, zinc gluconate, zinc pidolate, zinc sulphate, zinc chloride, zinc lactate or zinc phenoisulphonate; chlorhexidine and its salts; sodium bicarbonate; salicylic acid and its derivatives, such as 5-(n-octanoyl)salicylic acid; glycerol derivatives, such as, for example, caprylic/capric glycerides (Capmul MCM from Abitec), glycerol caprylate or caprate (Dermosoft GMCY and Dermosoft GMC respectively from Straetmans) or polyglyceryl-2 caprate (Dermosoft DGMC from Straetmans); biguanide derivatives, such as polyhexamethylene-biguanide salts; silver, zeolites or silver-free zeolites.

In order to improve the antiperspirant effectiveness of the composition, use may additionally be made of one or more water-soluble anionic polymers comprising a Bronsted acid, in particular those deriving from maleic acid and/or maleic anhydride which are described in Patent Application WO 02/49590.

Furthermore, "anti-perspirant salt or complex," as herein refers to any salt or complex which, by itself alone, has the effect of reducing or limiting the flow of sweat and/or absorbing human sweat. Examples of such anti-perspirant salt or complexes can be found in the OTC final monograph on Antiperspirant Actives and U.S. Patent Publications 20100196484, 20050031565, 20050238598, and 20110212144, the entire disclosures of which are incorporated herein by reference.

The antiperspirant salts or complexes are generally chosen from aluminium and/or zirconium salts or complexes. They are typically chosen from aluminium hydrohalides; aluminium zirconium hydrohalides, or complexes of zirconium hydroxychloride and of aluminium hydroxychloride, with or without an amino acid, such as those described in U.S. Pat. No. 3,792,068.

Mention may in particular be made, among the aluminium salts, of aluminium chlorohydrate in the activated or non-activated form, aluminium chlorohydrex, the aluminium chlorohydrex polyethylene glycol complex, the aluminium chlorohydrex propylene glycol complex, aluminium dichlorohydrate, the aluminium dichlorohydrex polyethylene glycol complex, the aluminium dichlorohydrex propylene glycol complex, aluminium sesquichlorohydrate, the aluminium sesquichlorohydrex polyethylene glycol complex, the aluminium sesquichlorohydrex propylene glycol complex or aluminium sulphate buffered with sodium aluminium lactate.

Mention may in particular be made, among aluminium zirconium salts, of aluminium zirconium octachloro-hydrate, aluminium zirconium pentachlorohydrate, aluminium zirconium tetrachlorohydrate or aluminium zirconium trichlorohydrate.

The complexes of zirconium hydroxychloride and of aluminium hydroxychloride with an amino acid are generally known under the name ZAG (when the amino acid is glycine). Mention may be made, among these products, of the aluminium zirconium octachlorohydrex glycine, aluminium zirconium pentachlorohydrex glycine, aluminium zirconium tetrathiorohydrex glycine and aluminium zirconium trichlorohydrex glycine complexes.

In order to further illustrate the present invention and the advantages thereof, the following specific examples and comparative example are given, it being understood that same are intended only as illustrative and in nowise limitative.

EXAMPLE 1

Microcapsules were prepared as follows:
A premix (I) comprises 25 g Polyvinyl pyrolidone K60) and 650 g water was prepared and the pH was adjusted to 10.0 using sodium hydroxide solution. Premix (II) comprises 300 g perfume to be encapsulated, 20 g Desmodur® W and 5 g Bayhydur® XP 2547 was prepared.

The two premixes were combined and emulsified at room temperature by means of a stirring device. The emulsification process was carried out to the desired droplet size. The pH of the emulsion was then adjusted to 8 using aqueous sodium hydroxide solution. Then 10 g of Lupasol® PR8515 solution was added in one step.

The reaction mixture was heated until the initiation was initiated.

The mixture was then cooled down to room temperature

An encapsulated perfume composition was obtained. The volume average capsule size distribution, obtained with light scattering measurements using a Malvern 2000S instrument, was D50=20 μm and D 90=50 μm with a shell weight 6% of total slurry weight composition. The solid content of the slurry was 40 weight %.

EXAMPLE 2

Encapsulated perfume compositions were prepared according to the methodology set forth in Example 1. The compositions contained 25% by weight of slurry of perfume compositions having ingredients specified in the Tables 1 through 5, below. The encapsulation process was described in Example 1 above. The amounts of aldehydes, non-aromatic cyclic perfumer ingredients and alkyl salicylates contained in the perfumes are shown (parts by weight of the perfume). The balance of the perfume is formed from other perfume ingredients commonly used in perfumery.

The compositions of the perfumes used in the example are listed in Tables 1 to 5. Under "ionone family" is meant ionones, irones, isoraldeines, damascones, damascenone, galbanone, and the like.

TABLE 1

| Perfume 1 composition | | | | |
|---|---|---|---|---|
| | Other ingredients | Non-aromatic cyclic ingredients | Alkyl salicyclates | Aldehydes |
| AROMATIC ESTERS | 3 | | | |
| NON-CYCLIC NON-AROMATIC ESTERS | 7 | | | |
| ALKYL CARBONATES | 1.5 | | | |
| DIMETHYL BENZYL CARBINYL ACETATE | 2 | | | |
| AGRUMEX | | 5 | | |
| PARA-ANISALDEHYDE | | | | 0.3 |
| TERPENE ALCOHOLS | 22 | | | |
| TERPINEOL | | 2 | | |
| TERPENYL ACETATE | | 2 | | |
| CITRONELLYL NITRILE | 1 | | | |
| IONONE FAMILY | | 10.7 | | |
| EUCALYPTOL | | 0.8 | | |
| FLOROSA | | 5 | | |
| GARDOCYCLENE | | 1 | | |
| INDOFLOR | 0.3 | | | |
| ISO E SUPER | | 10 | | |
| JASMONE FAMILY | | 1 | | |
| MAYOL | | 2 | | |
| AROMATIC ALCOHOL | 5 | | | |
| MENTHONE | | 0.3 | | |
| LACTONES | | 0.5 | | |
| HEXYL SALICYCLATE | | | 10 | |
| RADJANOL | 2 | | | |
| AROMATIC ETHERS | 0.3 | | | |

TABLE 1-continued

| Perfume 1 composition | | | | |
|---|---|---|---|---|
| | Other ingredients | Non-aromatic cyclic ingredients | Alkyl salicyclates | Aldehydes |
| ROSE OXIDE | | 0.3 | | |
| MACROCYCLIC MUSKS | | 5 | | |
| TOTAL | 44.1 | 45.6 | 10 | 0.3 |

TABLE 2

| Perfume 2 composition | | | | |
|---|---|---|---|---|
| | Other ingredients | Non-aromatic cyclic ingredients | Alkyl salicyclates | Aldehydes |
| AROMATIC ESTERS | 3 | | | |
| NON-CYCLIC NON-AROMATIC ESTERS | 8 | | | |
| ALKYL CARBONATES | 3 | | | |
| BORNYL ACETATE | | 3 | | |
| ALDEHYDE C 12 MNA | | | | 1 |
| FLORALOZONE | | | | 1 |
| TERPENE ALCOHOLS | 37 | | | |
| KETALS | 5 | | | |
| LEMONILE | 0 | | | |
| IONONE FAMILY | | 3 | | |
| CAMPHRE | | 2 | | |
| PHENOLS | 0 | | | |
| JASMACYCLENE | | 2 | | |
| ISO E SUPER | | 10 | | |
| AROMATIC ALCOHOL | 4 | | | |
| CIS-3-HEXENYL SALICYLATE | | | 3 | |
| HEXYL SALICYCLATE | | | 10 | |
| AROMATIC ETHERS | 0 | | | |
| MACROCYCLIC MUSKS | | 5 | | |
| TOTAL | 59 | 26 | 13 | 2 |

TABLE 3

| Perfume 3 composition | | | | |
|---|---|---|---|---|
| | Other ingredients | Non-aromatic cyclic ingredients | Alkyl salicyclates | Aldehydes |
| AROMATIC ESTERS | 8 | | | |
| NON-CYCLIC NON-AROMATIC ESTERS | 15 | | | |
| ALKYL CARBONATES | 2 | | | |
| PARA TERT BUTYL CYCLOHEXYL ACETATE | | 5 | | |
| AGRUMEX | | 8 | | |
| TERPENE ALCOHOLS | 11 | | | |
| FLORHYDRAL | | | | 2 |
| HELIOTROPINE | | | | 1 |
| IONONE FAMILY | | 8 | | |
| FLOROCYCLENE & HERBANATE | | 6 | | |
| INDOFLOR | | 4 | | |
| ISO E SUPER JASMONE FAMILY | | 2 | | |
| AROMATIC ALCOHOL | 1 | | | |
| LACTONES | | 5 | | |

TABLE 3-continued

Perfume 3 composition

| | Other ingredients | Non-aromatic cyclic ingredients | Alkyl salicyclates | Aldehydes |
|---|---|---|---|---|
| MACROCYCLIC MUSKS | 0.2 | 5 | | |
| PHENOLS | | | | |
| HEDIONE | | 16 | | |
| NECTARYL | | 2 | | |
| TOTAL | 38 | 60 | 0 | 2 |

TABLE 4

Perfume 4 composition

| | Other ingredients | Non-aromatic cyclic ingredients | Alkyl salicyclates | Aldehydes |
|---|---|---|---|---|
| NON-CYCLIC NON-AROMATIC ESTERS | 16.0 | | | |
| ALLYL CYCLOHEXYL PROPIONATE | | 2.0 | | |
| AGRUMEX | | 35.4 | | |
| ALCOHOLS | 3.0 | | | |
| LILIAL | | | | 5.0 |
| IONONE FAMILY | | 1.1 | | |
| JASMACYCLENE | | 20.0 | | |
| LACTONES | | 10.0 | | |
| CIS-3-HEXENYL SALICYLATE | | | 2.0 | |
| NECTARYL | | 5.0 | | |
| TOTAL | 19.0 | 73.5 | 2.0 | 5.0 |

TABLE 5

Perfume 5 composition

| | Other ingredients | Non-aromatic cyclic ingredients | Alkyl salicyclates | Aldehydes | Acetals(1) |
|---|---|---|---|---|---|
| AROMATIC ESTERS | 3.4 | | | | |
| NON-CYCLIC NON-AROMATIC ESTERS | 6.0 | | | | |
| ALKYL CARBONATES | 4.8 | | | | |
| DIMETHYL CARBINYL ACETATE | | | 6.0 | | |
| ALDEHYDE C 12 MNA | | | | 0.7 | |
| FLORALOZONE | | | | 1.4 | |
| TERPENE ALCOHOLS | 43.4 | | | | |
| METHYL PAMPLEMEOUSSE | | | | | 12.0 |
| CITRONELLYL NITRILE | 2.4 | | | | |
| LEMONILE | 0.2 | | | | |
| BORNYL ACETATE | | 2.4 | | | |
| INDOFLOR | | | | | |
| ISO E SUPER | | 12.0 | | | |
| CAMPHRE | | 1.7 | | | |
| SYLKOLIDE | 1.0 | | | | |
| AROMATIC ETHERS | 0.4 | | | | |

TABLE 5-continued

| Perfume 5 composition | | | | | |
|---|---|---|---|---|---|
| | Other ingredients | Non-aromatic cyclic ingredients | Alkyl salicyclates | Aldehydes | Acetals(1) |
| MACROCYCLIC MUSKS | 0.5 | | | | |
| MINOR COMPONENTS | 1.4 | | | | |
| TOTAL | 63.6 | 16.1 | 6.0 | 2.2 | 12.0 |

(1)2,2,2-trisubstituted acetals

TABLE 6

| Encapsulation performance of the perfume compositions | | | | | |
|---|---|---|---|---|---|
| | Aldehydes | Non-aromatic cyclic ingredients | Salicylates | 2,2,2-trisubstituted acetals | Encapsulation |
| Perfume 1 | 0.3 | 45.6 | 10 | | YES |
| Perfume 2 | 2.0 | 26.0 | 13.0 | | YES |
| Perfume 3 | 2.0 | 60.0 | 0 | | YES |
| Perfume 4 | 5.5 | 73.5 | 2.0 | | YES |
| Perfume 5 | 2.2 | 16.1 | 6.0 | 12.0 | YES |

EXAMPLE 3

A sensory test was carried out to compare the intensity of two samples of encapsulated perfume composition, formed according to the method of example 1, containing the same perfume but of two different sizes with D50 of 10 and 30 microns, overtime when in a roll-on deodorant base. The roll-on deodorants were tested on skin by a trained sensory panel. The products were assessed when freshly applied and then 2 hours, 6 hours and 10 hours after application. After 10 hours the products were also assessed after rubbing and directly from the skin.

The overall perceived intensity was assessed by the trained sensory panel using a 0-100 scale.

The panelists were instructed to smell their underarm immediately after sample application and then after 2 hours, 6 hours, 10 hours and 10 hours post rub through the t-shirt. 10 hours after application and after rub the under arms were also assessed directly from the skin.

For the rubbing assessment the panelists were instructed to move their left arm forward and their right arm backwards simultaneously whilst ensuring the upper arm rubs the side of their body and their lower arm is horizontally out in front of them. They were asked to make this movement four times in total.

Allocation of which sample was applied to which arm (left or right) was carried out according to a predetermined randomization and the panelists were always asked to assess their left underarm first. Each sample was assessed once by 21 panelists The data were analyzed using a Student T-test. The confidence level was 95%.

TABLE 7

| Capsule Diameter | Shell Weight (1) (%) | Time 0 Initial | Time 2 hours | Time 6 hours | Time 10 hours | Time 10 hours Post-rub |
|---|---|---|---|---|---|---|
| D50 = 10 microns | 15 | 28 | 22 | 19 | 13 | 18 |
| D50 = 30 microns | 15 | 38 | 30 | 23 | 13 | 20 |
| D50 = 30 microns | 19 | 37 | 27 | 23 | 14 | 20 |
| D50 = 30 microns | 23 | 28 | 23 | 20 | 13 | 18 |

(1) Percentage by weight based on the capsule weight (encapsulated material + shell material)

The results show a significant benefit of the capsules having a shell weight to diameter ratio of less than about 0.7.

EXAMPLE 4

A series of slurries containing polyurea capsules were formulated as disclosed in Table B and the extent of phase separation was measured after 1 week at 50° C. As apparent from the results, no phase separation is observed when using hydroxyethyl cellulose (Natrosol 250HX) at 0.4% by weight, and the slurry remains pourable. All other dispersion aids fail to stabilize the slurry over the test period.

Phase separation was measured by naked eye assessment and was expressed as the ratio of the height of the water phase to the total height of the slurry.

TABLE 8

| | 1 % | 2 % | 3 % | 4 % | 5 % | 6 % | Natrosol 250 HX (wt %) | Phase separation % | Viscosity (cps) |
|---|---|---|---|---|---|---|---|---|---|
| Slurry A | | | | | | 1.5 | 0 | 40 | |
| Slurry B | | | | | | | 0.4 | 0 | 2400 |
| Slurry C | 3 | | | | | | 0 | 10 | |
| Slurry D | | 3.5 | | | | | 0 | 10 | |
| Slurry E | | | 1.5 | | | | 0 | 15 | |
| Slurry F | | | | 0.5 | | | 0 | 30 | |
| Slurry G | | | | | 2 | | 0 | 40 | |

1 = National 465;
2 = Starch B990;
3 = Tinovis CD;
4 = Ultragel 300;
5 = Rheocare TTA;
6 = Purity W

EXAMPLE 5

90 g of an encapsulated perfume composition formed according to the procedure of example 1 was formed as a slurry. To this slurry was added 9 g of Capsul E (@ 23% in water) and 1 g of silica (Syloid FP 244). The slurry was agitated 30 min at 250 rpm and spray dried in a spray dryer (labplant) using an atomizer. The inlet temperature was 180° C. and the outlet temperature was 90° C. A free flowing powder was obtained with a D50 of 30 microns and 65% fragrance loading. The residual water constant was 4% by weight and the surface oil was 0.8% by weight

The invention claimed is:

1. An encapsulated perfume composition comprising one or more polyurea capsules having a volume average diameter of 20 to 90 microns, and a capsule shell weight, which is 5 to 40% by weight of the total weight of the capsules (core+shell), wherein the nominal rupture stress of the polyurea capsules is in the range of 0.1 to 2 MPa.

2. An encapsulated perfume composition according to claim 1 wherein the ratio of the shell weight, expressed as a percentage of the total weight of the capsules (core+shell) to the capsule volume average diameter, expressed in microns, is 0.7 microns$^{-1}$ or less.

3. An encapsulated perfume composition according to claim 1, wherein the encapsulated perfume comprises at least 60% by weight of perfume ingredients having solubility in water of 15000 ppm or less.

4. An encapsulated perfume composition according to claim 1, wherein the capsules contain no encapsulated solvent.

5. An encapsulated perfume composition according to claim 1 in the form of a powder comprising a silica flow aid, wherein the silica has a particle size of 1 to 8 microns.

6. An encapsulated perfume composition according to claim 4, wherein the silica flow aid is SYLOID FP 244.

7. A method of forming an encapsulated perfume composition according to claim 4, said method comprising the step of: dispersing the silica in the encapsulated perfume composition in the form of a slurry, and thereafter dehydrating the slurry.

8. A method according to claim 7, wherein the slurry is dehydrated by spray drying.

9. A leave-on personal care product comprising an encapsulated perfume composition according to claim 1.

10. A leave-on product according to claim 9 in the form of a deodorant product.

11. A leave on product according to claim 9 in the form of an anti-perspirant.

12. An encapsulated perfume composition according to claim 1, wherein the nominal rupture stress of the polyurea capsules is in the range of 0.2 to 1.5 Mpa.

13. An encapsulated perfume composition according to claim 1, wherein the nominal rupture stress of the polyurea capsules is in the range of 0.4 to 1 MPa.

* * * * *